(12) United States Patent
Haught et al.

(10) Patent No.: US 8,962,057 B2
(45) Date of Patent: Feb. 24, 2015

(54) METHODS FOR IMPROVING TASTE AND ORAL CARE COMPOSITIONS WITH IMPROVED TASTE

(75) Inventors: John Christian Haught, West Chester, OH (US); Koti Tatachar Sreekrishna, Mason, OH (US); Yakang Lin, Liberty Township, OH (US); Lowell Alan Sanker, Mason, OH (US)

(73) Assignee: The Procter & Gamble Company, Cincinnati, OH (US)

(*) Notice: Subject to any disclaimer, the term of this patent is extended or adjusted under 35 U.S.C. 154(b) by 525 days.

(21) Appl. No.: 12/763,933

(22) Filed: Apr. 20, 2010

(65) Prior Publication Data

US 2010/0278991 A1 Nov. 4, 2010

Related U.S. Application Data

(60) Provisional application No. 61/173,711, filed on Apr. 29, 2009, provisional application No. 61/177,457, filed on May 12, 2009.

(51) Int. Cl.

| | | |
|---|---|---|
| A61K 8/34 | (2006.01) |
| A61Q 11/00 | (2006.01) |
| A61K 8/19 | (2006.01) |
| A61K 8/22 | (2006.01) |
| A61K 8/27 | (2006.01) |
| A61K 8/35 | (2006.01) |
| A61K 8/42 | (2006.01) |
| A61K 8/49 | (2006.01) |
| A61K 8/97 | (2006.01) |

(52) U.S. Cl.
CPC ... A61K 8/19 (2013.01); A61K 8/22 (2013.01); A61K 8/27 (2013.01); A61K 8/347 (2013.01); A61K 8/35 (2013.01); A61K 8/42 (2013.01); A61K 8/49 (2013.01); A61K 8/97 (2013.01); A61Q 11/00 (2013.01)
USPC .............. 426/532; 426/538; 424/401; 424/52

(58) Field of Classification Search
CPC ........... A61K 8/347; A61K 8/49; A61K 8/97; A61K 8/42; A61K 8/22; A61K 8/27; A61K 8/35; A61K 8/19; A61Q 11/00
See application file for complete search history.

(56) References Cited

U.S. PATENT DOCUMENTS

| 3,863,006 | A | * | 1/1975 | Hodosh ........................ 424/49 |
|---|---|---|---|---|
| 4,649,044 | A | | 3/1987 | Gomi |
| 4,774,076 | A | | 9/1988 | Gomi |
| 5,015,467 | A | * | 5/1991 | Smitherman ................ 424/52 |
| 5,035,882 | A | | 7/1991 | Hussein |
| 5,330,749 | A | * | 7/1994 | Giacin et al. ................ 424/49 |
| 5,788,982 | A | | 8/1998 | Nadoolman |
| 6,042,812 | A | | 3/2000 | Sanker |
| 6,328,982 | B1 | | 12/2001 | Shiroyama |
| 6,570,010 | B2 | | 5/2003 | Ishida |
| 6,579,543 | B1 | | 6/2003 | McClung |
| 6,702,999 | B2 | | 3/2004 | Lawlor |
| 6,703,000 | B2 | | 3/2004 | Ning |
| 6,706,256 | B2 | | 3/2004 | Lawlor |
| 6,706,277 | B2 | | 3/2004 | Day |
| 6,719,962 | B2 | | 4/2004 | Day |
| 6,726,897 | B2 | | 4/2004 | Lawlor |
| 6,730,291 | B2 | | 5/2004 | Lawlor |
| 6,780,443 | B1 | | 8/2004 | Nakatsu |
| 6,838,106 | B2 | | 1/2005 | Kumamoto |
| 6,890,567 | B2 | | 5/2005 | Nakatsu |
| 6,899,901 | B2 | | 5/2005 | Nakatsu |
| 7,445,769 | B2 | | 11/2008 | Holme |
| 2002/0054893 | A1 | | 5/2002 | Ishida |
| 2003/0017209 | A1 | | 1/2003 | Parikh |
| 2005/0042183 | A1 | | 2/2005 | Kato |
| 2005/0129721 | A1 | | 6/2005 | Ishida |
| 2005/0181022 | A1 | | 8/2005 | Cai |
| 2005/0260266 | A1 | | 11/2005 | Gebreselassie |
| 2006/0024244 | A1 | | 2/2006 | Gebreselassie |
| 2006/0024245 | A1 | | 2/2006 | Gebreselassie |
| 2006/0034897 | A1 | | 2/2006 | Boghani |
| 2006/0045934 | A1 | | 3/2006 | Kabse |
| 2006/0051456 | A1 | | 3/2006 | Kabse |
| 2006/0062872 | A1 | | 3/2006 | Gebreselassie |

(Continued)

FOREIGN PATENT DOCUMENTS

| EP | 0137419 B1 | 4/1985 |
|---|---|---|
| EP | 0697458 B1 | 2/1996 |

(Continued)

OTHER PUBLICATIONS

Smart, Jerman, Gunthorpe, Brough, Ranson, Cairns, Hayes, Randall, Davis, Characterization using FLIPR of human vanilloid VR1 receptor pharmacology, European Journal of Pharmacology 417, pp. 51-58 (2001).

Liu, Abell, Development and validation of a platelet calcium flux assay using a fluorescent imaging plate reader, Analytical Biochemistry 357, pp. 216-224 (2006).

Ryu, A Review on the Possible Gating Mechanism of TRPV1 channel, Biowave, 2008, pp. 1-39, vol. 10 No. 14, Biological Research Information Center.

Riera, Vogel, Simon, Le Coutre, Artificial Sweeteners and Salts-Producing a Metallic Taste sensation Activate TRPVI Receptors, Am. J. Physiol. Regulatory Integrative Comp. Physiol, Jun. 13, 2007, pp. 626-634, 293.

(Continued)

*Primary Examiner* — Kortney L Klinkel
*Assistant Examiner* — Lisbeth C Robinson
(74) *Attorney, Agent, or Firm* — Alexandra S. Anoff; Carrie Morgan

(57) ABSTRACT

Provided herein are compositions and methods relating to oral care compositions with improved taste. One such method includes providing an oral care composition comprising a metal salt, a peroxide, an antimicrobial agent, a bad breath reduction agent, a surfactant, or a combination thereof and adding to the oral care composition a TRPV1 activator and/or vanitrope.

16 Claims, No Drawings

(56) References Cited

U.S. PATENT DOCUMENTS

| | | |
|---|---|---|
| 2006/0159818 A1 | 7/2006 | Kunieda |
| 2006/0160713 A1 | 7/2006 | Sekine |
| 2006/0177383 A1 | 8/2006 | Gebreselassie |
| 2006/0177384 A1 | 8/2006 | Brown |
| 2006/0193896 A1 | 8/2006 | Boghani |
| 2006/0263413 A1 | 11/2006 | Boghani |
| 2006/0263472 A1 | 11/2006 | Boghani |
| 2006/0263473 A1 | 11/2006 | Boghani |
| 2006/0263477 A1 | 11/2006 | Boghani |
| 2006/0263478 A1 | 11/2006 | Boghani |
| 2006/0263479 A1 | 11/2006 | Boghani |
| 2006/0263480 A1 | 11/2006 | Boghani |
| 2006/0286202 A1 | 12/2006 | Boghani |
| 2006/0286203 A1 | 12/2006 | Boghani |
| 2007/0036733 A1 | 2/2007 | Spence |
| 2007/0042078 A1 | 2/2007 | Miladinov |
| 2007/0042079 A1 | 2/2007 | Miladinov |
| 2007/0065394 A1 | 3/2007 | Pinney |
| 2007/0098845 A1 | 5/2007 | Soper |
| 2007/0104829 A1 | 5/2007 | Soper |
| 2007/0148103 A1 | 6/2007 | Harvey |
| 2007/0178187 A1 | 8/2007 | Shetty |
| 2007/0178188 A1 | 8/2007 | Shetty |
| 2007/0190090 A1 | 8/2007 | Brown |
| 2007/0221236 A1 | 9/2007 | Kiefer |
| 2007/0225378 A1 | 9/2007 | Ishida |
| 2007/0231435 A1 | 10/2007 | Ream |
| 2007/0237725 A1 | 10/2007 | Tancredi |
| 2007/0298061 A1 | 12/2007 | Boghani |
| 2008/0038386 A1 | 2/2008 | Moza |
| 2008/0089850 A1 | 4/2008 | Haskel |
| 2008/0138465 A1 | 6/2008 | Soper |
| 2008/0153845 A1 | 6/2008 | Palmer |
| 2008/0160116 A1 | 7/2008 | Li |
| 2008/0194518 A1 | 8/2008 | Mookerjee |
| 2008/0221003 A1 | 9/2008 | Meine |
| 2008/0233233 A1 | 9/2008 | Soper |
| 2008/0253973 A1 | 10/2008 | Tamarkin |
| 2008/0253976 A1 | 10/2008 | Scott |
| 2009/0004360 A1 | 1/2009 | Bingley |
| 2009/0010958 A1 | 1/2009 | Pinney |

FOREIGN PATENT DOCUMENTS

| | | |
|---|---|---|
| EP | 0750849 B1 | 1/1997 |
| EP | 0988852 B1 | 4/2004 |
| EP | 1459733 A1 | 9/2004 |
| EP | 1167435 B1 | 12/2004 |
| EP | 1514539 A2 | 3/2005 |
| EP | 1561476 A1 | 8/2005 |
| EP | 1393716 B1 | 3/2006 |
| EP | 1496095 B1 | 12/2006 |
| EP | 1186289 B1 | 2/2007 |
| EP | 1121927 B1 | 12/2010 |
| GB | 2068229 A | 8/1981 |
| JP | 57082308 | 5/1982 |
| JP | 1203316 A | 8/1989 |
| JP | 11093067 | 4/1999 |
| JP | 11093071 | 4/1999 |
| JP | 2000044924 | 2/2000 |
| JP | 2000-302655 | 10/2000 |
| JP | 2000302655 | 10/2000 |
| JP | 2000302655 A * | 10/2000 |
| JP | 2002176950 | 6/2002 |
| JP | 2002179517 | 8/2002 |
| WO | WO9921425 A1 | 5/1999 |
| WO | WO02091847 A1 | 11/2002 |
| WO | WO03055459 | 7/2003 |
| WO | WO2005115325 A1 | 12/2005 |
| WO | WO2006130710 A1 | 12/2006 |
| WO | WO2006137556 A1 | 12/2006 |
| WO | WO2006137958 A1 | 12/2006 |
| WO | WO2006137959 A1 | 12/2006 |
| WO | WO2007004740 A1 | 1/2007 |
| WO | WO2007042472 A1 | 4/2007 |
| WO | WO2007113855 A1 | 10/2007 |
| WO | WO2007145663 A1 | 12/2007 |

OTHER PUBLICATIONS

Prescott, Stevenson, Desensitization to Oral Zingerone Irritation: Effects of Stimulus Parameters, Physiology & Behavior, Jan. 26, 1996, pp. 1473-1480, vol. 60 No. 6, Elsevier Science Inc.

Gavva, Klionsky, Qu, Shi, Tamir, Edenson, Zhang, Viswanadhan, Toth, Pearce, Vanderah, Porreca, Blumberg, Lile, Sun, Wild, Louis, Treanor, Molecular Determinants of Vanilloid Sensitivity in TRPV1, JBC Papers in Press, Mar. 2, 2004, pp. 1-40, Manuscript M312577200, The American Society for Biochemistry and Molecular Biology Inc.

Rami, Gunthorpe, The Therapeutic Potential of TRPV1 (VR1) Antagonists: Clinical Answers Await, Drug Discovery Today: Therapeutic Strategies, 2004, pp. 97-104, vol. 1 No. 1 Elsevier.

Chung, Guler, Caterina, TRPV1 Shows Dynamic Ionic Selectivity During Agonist Stimulation, Nature Neuroscience, 2008, pp. 555-564, vol. 11 No. 5, Nature Publishing Group.

Shin, Kim, Chung, Jeong, Zingerone as an Antioxidant Against Peroxynitrile, Journal of Agricultural and Food Chemistry, Aug. 19, 2005, pp. 7617-7622, 53 American Chemical Society.

Clapham, TRPV Channels, http://clapham.tch.harvard.edu/publications/pdf/TRPV%20Vanilloid%20Family.pdf.

* cited by examiner

METHODS FOR IMPROVING TASTE AND ORAL CARE COMPOSITIONS WITH IMPROVED TASTE

CROSS REFERENCE

This application claims the benefit of provisional application Ser. No. 61/173,711, filed on Apr. 29, 2009, and of provisional application Ser. No. 61/177,457 filed on May 12, 2009, each of which is incorporated by reference in its entirety herein.

FIELD OF THE INVENTION

The present invention is directed to oral care compositions with improved taste and methods of improving the taste of oral care compositions.

BACKGROUND OF THE INVENTION

People are always looking for ways to improve their smile and the health of their teeth and oral cavity. The first step on this journey for many is the use of oral care compositions like toothpaste and rinse. The benefits achieved from the use of those types of products cover a broad range from cosmetic benefits, like whitening and fresh breath, to health benefits, like reduced tartar. Unfortunately, many components used in oral care compositions, including the agents giving the desired benefits, often have a negative impact on the overall taste of the product. As such, there is a need for methods which provide improved flavor in oral care compositions and oral care compositions with improved flavor.

SUMMARY OF THE INVENTION

In one embodiment, the present invention is directed to a method for improving taste of an oral care composition. The method includes mixing a TRPV1 activator and a bad taste agent selected from the group consisting of: a metal salt, a peroxide, an antimicrobial agent, a bad breath reduction agent, a surfactant, and combinations thereof, to form an oral care composition.

In another embodiment, the present invention is directed to a method for improving taste of an oral care composition where the method includes mixing vanillyl butyl ether and a bad taste agent comprising a zinc salt, stannous salt, a potassium salt, copper salt, or a combination thereof, to form an oral care composition, wherein the vanillyl butyl ether is present in an amount of about 0.001% to about 0.025% by weight of the oral care composition.

In another embodiment, the present invention is directed to a method for improving taste of an oral care composition where the method includes mixing vanitrope and a bad taste agent comprising a metal salt, a peroxide, or a combination thereof, to form an oral care composition, wherein the vanitrope is present in an amount of about 0.01% to about 0.4% by weight of the oral care composition.

It is believed that these as well as other embodiments of the present invention will be better understood from the following description.

DETAILED DESCRIPTION OF THE INVENTION

Definitions

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

As used herein, the word "about" means +/−10 percent.

As used herein, the word "include," and its variants, are intended to be non-limiting, such that recitation of items in a list is not to the exclusion of other like items that may also be useful in the materials, compositions, devices, and methods of this invention.

By "oral care composition" is meant a product, which in the ordinary course of usage, is not intentionally swallowed for purposes of systemic administration of particular therapeutic agents, but is rather retained in the oral cavity for a time sufficient to contact dental surfaces and/or oral tissues. The oral care composition may be in various forms including toothpaste, dentifrice, tooth gel, subgingival gel, mouth rinse, mousse, foam, mouth spray, lozenge, chewable tablet, chewing gum or denture care product. The oral care composition may also be incorporated onto strips or films for direct application or attachment to oral surfaces.

The term "dentifrice", as used herein, includes paste, gel, or liquid formulations unless otherwise specified. The dentifrice can be in a dual phase form, like a striped paste for example, and can also be used as a regimen.

The term "bad taste agent" as used herein, refers to a component in an oral care composition which gives an adverse taste to a user, for example, a metallic taste or an astringent taste, or an adverse sensation, for example, a feeling of dry mouth.

The term "teeth", as used herein, refers to natural teeth as well as artificial teeth or dental prosthesis.

The term "TRPV1" as used herein refers to the transient receptor potential vanilloid receptor 1 which is a ligand-gated, non-selective cation channel preferentially expressed on small-diameter sensory neurons and detects noxious as well as other substances.

The term "TRPV1 activator" as used herein refers to any component which at a concentration of 1 mM gives a calcium flux count of at least 1000 counts above the background level of calcium present in the cell according to the FLIPR method as discussed herein. The term "count" is defined as the change in fluorescence of the transfected cell lines due to the influx of calcium across the cell membrane, which reacts with the calcium sensitive dye present within the cells.

The term "TRPV1 enhancer" as used herein refers to any component that boosts the calcium flux activity of a compound that directly activates TRPV1, but does not directly activate TRPV1.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Oral Care Compositions and Methods

It is highly desirable that consumer products for use in cleaning and care of the oral cavity impart a fresh and clean feeling as this provides consumers with a signal of continuing freshness and cleanliness. In addition to the feeling of cleanliness, consumers also want to experience the benefits of oral care actives like anti-tartar agents, for example, through their oral care regimen. The ability to formulate a consumer acceptable oral care composition, however, raises challenges as many of the components used to impart a flavor, deliver a benefit, or that are part of the base for the oral care composition add unwanted tastes and/or sensations along with the targeted benefit for which they are added. Thus, formulating oral care compositions can be a balancing act between acceptable flavor and acceptable benefits.

As will be seen below, many of the components which can be used to formulate an oral care composition provide an off taste and thus make formulating a consumer acceptable product a challenge. It has now been discovered that the addition of certain components to an oral care composition can reduce many of the off tastes associated with many of the components discussed below and thus improve the taste. These taste improving components include, for example, TRPV1 activators and vanitrope.

The first group of components which will help to improve taste in an oral care composition are Transient Receptor Potential Vanilloid 1 (TRPV1) activators. TRPV1 is a ligand-gated, non-selective cation channel preferentially expressed on small diameter sensory neurons. In looking at this receptor, it was discovered that activation of this receptor caused a surprising effect. By adding a TRPV1 activator to an oral care composition with an off tasting component, the user of the composition experienced an improved taste over an oral care composition without the TRPV1 activator. Thus, the TRPV1 activator is working to off-set the bad taste associated with many components used in oral care compositions.

In order to determine whether TRPV1 is activated, the intracellular calcium ion ($Ca^{+2}$) levels in TRPV1 receptors is measured. HEK-23 (human embryonic kidney) cells stably transfected with human TRPV1 are grown in 15 ml growth medium [high glucose DMEM (Dulbecco's Modification of Eagle's Medium) supplemented with 10% FBS (fetal bovine serum), 100 µg/ml Penicillin/streptomycin, 100 µg/ml G418] in a 75 $Cm^2$ flask for 3 days at 33° C. in a mammalian cell culture incubator set at 5% $CO_2$. Cells are detached with addition of 10 ml of PBS (phosphate buffered saline) by hand shaking gently. Cells are transferred to a 50 ml tube and centrifuged at 850 rpm for 3 minutes to remove PBS. After centrifugation, a pellet of cells is formed in the bottom of the tube separating them from the supernatant solution. The supernatant is discarded and the cell pellet is suspended in 1 ml of fresh growth medium to which 5 µl (12.5 µg) of Fluo-4 AM (Molecular Probes, Inc.) calcium indicator is added and incubated for 30 min with gentle shaking. Fluo-4 is a fluorescent dye used for quantifying cellular $Ca^{2+}$ concentrations in the 100 nM to 1 microM range. At the end of the 30 minutes, 45 ml of assay buffer [1×HBSS (Hank's Balanced Salt Solution), 20 mM HEPES (4-(2-Hydroxyethyl)-1-piperazineethanesulfonic acid)] is added to wash cells and the resulting combination is then centrifuged at 850 rpm for 3 minutes to remove excess buffer and Fluo-4 AM calcium indicator.

The pellet cells are re-suspended in 10 ml assay buffer and 90 µl aliquots (~50,000 cells) per well delivered to a 96-well assay plate containing 10 µl of test compounds (1 mM in assay buffer, final concentration 100 µM) or buffer control and incubated at room temperature for 30 minutes. After 30 minutes, the plate is placed into a fluorometric imaging plate reader (FLIPR[384] from Molecular Devices) and basal fluorescence recorded (excitation wave length 488 nm and emission wave length 510 nm). The FLIPR assay is an accepted method for detecting changes in intracellular calcium concentration. Then 20 µl of the molecule being tested as a TRPV1 activator is added and fluorescence recorded. For determining the direct effect of test compounds on TRPV1, fluorescence is measured immediately after addition of each compound. Additional discussion of the FLIPR method can be found in Smart et al., *Characterization using FLIPR of human vanilloid VR1 receptor pharmacology*, European Journal of Pharmacology 417, 51-58 (2001) and Liu et al., *Development and validation of a platelet calcium flux assay using a fluorescent imaging plate reader*, Analytical Biochemistry 357, 216-224 (2006).

TRPV1 responds to, for example, both noxious and painful stimuli. A noxious stimulus would include those which give a burning (i.e. hot) sensation. A chart below lists some TRPV1 activators which fall into this class and give a burning sensation as measured on the standard Scoville hotness scale.

| Compound | 'Hotness' (as log Scoville Units) |
| --- | --- |
| Dihydrocapsaicin | 7.2 |
| Capsaicin | 7.2 |
| NorhydroCapsaicin | 7.0 |
| HomodihydroCapsaicin | 6.9 |
| HomoCapsaicin | 6.9 |
| Vanillyl Butyl Ether | 5.7 |
| Piperine | 5.3 |
| 6-Shoagol | 5.1 |
| 6-Gingerol | 4.9 |
| Allicin | 4.0 |
| Zingerone | <4.0 |

Since many of these compounds are derived from natural sources, they often retain the inherent pungency of the source material when used at levels to exert a warming effect. For example, piperine is peppery, capsaicin is like red peppers, and zingerone retains the pungency of ginger. This also holds true for synthetic compounds, like vanillyl butyl ether, as described in U.S. Pat. No. 6,570,010B2. Interestingly, the use of TRPV1 activators, like those above, at an amount below that which triggers a burning effect gives a reduction in off-taste and a product in which the consumer can detect the improved taste. The use of a level which triggers a burning effect results in the consumer noticing the burning sensation and not, necessarily, an improved flavor. In one embodiment, a TRPV1 activator will be added in an amount of about 0.0001% to about 0.1% by weight of the oral care composition. However, the level of activation of TRPV1 is related to the level of hotness of the activator. Thus, the level of TRPV1 activator used will depend on the strength of its hotness. For example, vanillyl butyl ether (which has an activation level of approximately 14942.84 calcium ions at a concentration of 1 mM) will generally be used at an amount of about 0.025% or below while capsaicin (which has an activation level of about 14127.16 calcium ions at a much lower concentration level of 300 nM) will be used at an amount of about 0.009% or below. Thus a much smaller concentration of capsaicin (300 nM) gives nearly the same level of activation as a much higher concentration of VBE (1 mM) and thus can be used in smaller quantities.

In addition to its role as a noxious substance detector, it is believed that the activation of TRPV1 also has some downstream affects. Specifically, without being limited by theory, it is believed that activation of TRPV1 causes changes in other taste receptors, specifically PKD1L3, PKD2L1, and the TAS2R family of receptors. It is believed the changes in the TAS2R16, TAS2R38, PKD2L1, and PKD1L3 receptors also contribute to the improvement in taste.

Interestingly, some of the compounds which give an off taste also affect the activity of TRPV1, but at a very low level (i.e. below that needed to be a TRPV1 activator). Without being limited by theory, for those components which render an off taste in oral care compositions and which affect the TRPV1 receptor activity but do not rise to the level of an activator, it is believed the TRPV1 activators out compete these components for binding of the TRPV1 receptor. This prevents the off-taste components from spreading any off-taste through TRPV1 or any downstream activities caused by the binding of the off taste component to TRPV1.

In light of the above, according to one embodiment of the invention, an oral care composition comprising a bad taste agent and a TRPV1 activator(s) would have an improved taste. Additionally, in one embodiment, a method of improving the taste of an oral care composition comprises mixing a TRPV1 activator and a bad taste agent selected from the group consisting of: a metal salt, a peroxide, an antimicrobial agent, a bad breath reduction agent, a surfactant, and combinations thereof, to form an oral care composition.

In one embodiment, the TRPV1 activator comprises vanillyl butyl ether, zingerone, capsaicin, capsiate, shoagol, gingerol, piperine, or a combination thereof. In a further embodiment, the TRPV1 activator comprises vanillyl butyl ether. In one embodiment, the vanillyl butyl ether is added at an amount of about 0.001% to about 0.25% by weight of the oral care composition. In another embodiment, the vanillyl butyl ether is added in an amount of from about 0.002% to about 0.02% by weigh of the oral care composition.

In another embodiment, a method for improving taste of an oral care composition comprises mixing vanillyl butyl ether and a bad taste agent comprising a zinc salt, stannous salt, a potassium salt, copper salt, or a combination thereof, to form an oral care composition, wherein the vanillyl butyl ether is present in an amount of about 0.001% to about 0.025% by weight of the oral care composition. In a further embodiment, the oral care composition or method further comprises adding vanitrope, zingerone, or a combination thereof to the oral care composition. In one embodiment, the zingerone is added at an amount from about 0.01% to about 0.015%. In another embodiment, the vanitrope is added at an amount from about 0.01% to about 0.015%.

Additionally, some compounds have been found to enhance the effect of TRPV1 activators, even though these enhancers do not activate TRPV1 on their own. For examples, see the chart below, where the enhancer is added after a TRPV1 actovator (capsaicin) to determine if additional activation occurs.

| Compound Name | CAS # | % Enhancement |
| --- | --- | --- |
| delta-damascone | 57378-68-4 | 28.53 |
| Alpha-Damascone | 43052-87-5 | 28.1 |
| Geranyl Butyrate | 106-29-6 | 23.46 |
| 2-Octanone | 111-13-7 | 19.87 |
| Furfural | 98-01-1 | 19.29 |
| Alpha-Ionone | 127-41-3 | 18.84 |
| 2,6-Dimethyl-5-Heptenal | 106-72-9 | 17.5 |
| Tetrasodium Pyrophosphate | 7722-88-5 | 15.62 |
| Alpha, Alpha Dimethylphenethyl Acetate | 151-05-3 | 14.64 |
| Phenylacetaldehyde Dimethyl Acetal | 101-48-4 | 14.07 |
| Kephalis | 36306-87-3 | 13.74 |
| Linalool Oxide | 1365-19-1 | 13.67 |
| carvyl acetate | 97-42-7 | 12.83 |
| Farnesene | 502-61-4 | 12.33 |
| Trans-2-Hexenyl Acetate | 2497-18-9 | 10.62 |
| Heptyl Alcohol | 111-70-6 | 10.16 |

In a separate test, the TRPV1 activator (VBE) and the enhancer are added together. Here, without being limited by theory, it appears there surprisingly is an additional affect on the activation of the TRPV1 activator when the enhancer is added at the beginning. See the chart below.

| VBE Level | Enhancer | Enhancer Level | Percent Enhancement When combined with 3.5 microMolar VBE |
| --- | --- | --- | --- |
| 3.5 micro-Molar | Alpha, Alpha Dimethyl-phenethyl Acetate | 1000 microMolar | 420% |
| | | 200 microMolar | 410% |
| | | 100 microMolar | 310% |
| | | 50 microMolar | 300% |
| 3.5 micro-Molar | Farnescene | 1000 microMolar | 400% |
| | | 200 microMolar | 175% |
| | | 100 microMolar | 100% |
| | | 50 microMolar | 25% |

The use of an enhancer will provide a further boost to improving the taste of an oral care composition and can reduce the amount of TRPV1 activator required. The level of enhancement can be used to help determine the effect of the booster and any desired reduction in TRPV1 activator. For example, in one embodiment vanillyl butyl ether would be used at 0.012%, but with the enhancer delta damascene at 0.003%, VBE could be used at 0.008% to achieve the same effect as without the enhancer.

Thus, in one embodiment, an oral care composition or a method of improving taste of an oral care composition further comprises adding a TRPV1 enhancer to the oral care composition. In a further embodiment, the TRPV1 enhancer is selected from the group consisting of damascone, geranyl butyrate, 2-octanone, furfural, ionone, 2,6-dimethyl-5-heptenal, tetrasodium pyrophosphate, alpha dimethyl phenethyl acetate, phenylacetaldehyde dimethyl acetal, kephalis, linalool oxide, carvyl acetate, farnesene, trans-2-hexenyl acetate, heptyl alcohol, and combinations thereof.

Although not considered to be a TRPV1 activator, vanitrope also has the ability to reduce the off taste associated with at least some of the components listed above. Vanitrope is a eugenol derivative which has a vanilla note. Without being limited by theory, it is believed that Vanitrope likely modulates the taste receptors aforementioned directly, without the assistance of the TRPV1 activation.

In light of the above, an oral care composition comprising an oral care component which gives a bad taste and vanitrope would have an improved taste. Additionally, in one embodiment, the present invention is directed to a method for improving taste of an oral care composition, comprising mixing vanitrope and a bad taste agent comprising a metal salt, a peroxide, or a combination thereof, to form an oral care composition, wherein the vanitrope is present in an amount of about 0.01% to about 0.4% by weight of the oral care composition.

In one embodiment, the metal salt comprises a zinc salt, stannous salt, potassium salt, copper salt, or a combination thereof. In another embodiment, the peroxide is selected from the group consisting hydrogen peroxide, carbamide peroxide, calcium peroxide, sodium peroxide, and combinations thereof. In another embodiment, the vanitrope is added in an amount from about 0.05% to about 0.15% by weight of the oral care composition. In an additional embodiment, the potassium salt comprises potassium nitrate and is present in an amount of from about 0.01% to about 5.0% by weight of the oral care composition. In another embodiment, the zinc salt comprises zinc citrate and is present in an amount from about 0.05% to about 5.0% by weight of the oral care composition.

In an additional embodiment, the combination of vanitrope, zingerone, and vanillyl butyl ether can be used to give an improved taste in oral care compositions. Thus, in one embodiment, an oral care composition with an improved taste comprises vanitrope, zingerone, and vanillyl butyl.

The order of addition of the TRPV1 activators and/or vanitrope is not critical. Thus, the TRPV1 activators and/or vanitrope can be added in with the oral care components at the time of making the oral care composition or at some point after the oral care composition is complete.

Oral Care Composition

Oral care compositions are often made up of a combination of components which can include carrier materials, surfactants, flavors, colorants, sensates, actives, and other additives.

Carrier Material

Carrier materials generally represents anywhere from about 5% to about 80% of the oral care composition by weight. Examples of materials which can act as a carrier material include water, glycerin, sorbitol, polyethylene glycols having a molecular weight of less than about 50,000, propylene glycol and other edible polyhydric alcohols, ethanol, or combinations thereof. Of these carrier materials, examples of some which provide an unwanted taste within an oral care composition include, for example, propylene glycol and/or ethanol. The unwanted tastes often associated with these types of materials are bitterness, burning, astringency, and/or earthy or dirty tastes.

Surfactants

Another component of an oral care composition can include surfactants. Surfactants are generally included in an oral care composition in a range of about 1% to about 15%. The surfactant may be anionic, nonionic, amphoteric, zwitterionic, cationic, or combinations thereof. Anionic surfactants useful herein include, for example, the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants include sarcosinates, such as sodium lauroyl sarcosinate, taurates, sodium lauryl sulfoacetate, sodium lauroyl isethionate, sodium laureth carboxylate, and sodium dodecyl benzenesulfonate. Combinations of anionic surfactants can also be employed. Many suitable anionic surfactants are disclosed by Agricola et al., U.S. Pat. No. 3,959,458. In varying embodiments, the present compositions comprise an anionic surfactant at a level of from about 0.025% to about 9%, from about 0.05% to about 5%, or from about 0.1% to about 1%.

Another class of anionic surfactants useful here are alkyl phosphates. The surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

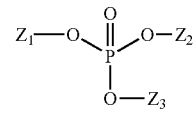

Some other agents include alkyl or alkenyl phosphate esters represented by the following structure:

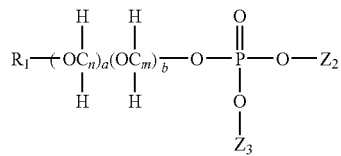

wherein $R_1$ represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; $Z_2$ and $Z_3$ may be identical or different, each represents hydrogen, alkali metal, ammonium, protonated alkyl amine or protonated functional alkyl amine such as an alkanolamine, or a $R_1-(OC_nH_{2n})_a(OC_mH_{2m})_b-$ group. Examples of suitable agents include alkyl and alkyl(poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol)phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates.

Another suitable surfactant is one selected from the group consisting of sarcosinate surfactants, isethionate surfactants and taurate surfactants. In one embodiment, an alkali metal or ammonium salts of these surfactants are used. Examples of those sodium and potassium salts include following: lauroyl sarcosinate, myristoyl sarcosinate, palmitoyl sarcosinate, stearoyl sarcosinate and oleoyl sarcosinate, or combinations thereof. Of these anionic surfactants, examples of some which provide an unwanted taste within an oral care composition include, for example, SLS, lauroyl sarcosinate, and/or fatty alcohols or acids associated with natural based surfactants. The unwanted tastes often associated with these surfactants are soapy, chemical, and/or artificial.

Zwitterionic or amphoteric surfactants useful in oral care compositions include derivatives of aliphatic quaternary ammonium, phosphonium, and sulfonium compounds, in which the aliphatic radicals can be straight chain or branched, and one of the aliphatic substituents contains from about 8 to 18 carbon atoms and one contains an anionic water-solubilizing group, e.g., carboxy, sulfonate, sulfate, phosphate or phosphonate. Suitable betaine surfactants are disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine (CADB), and lauramidopropyl betaine. Of these surfactants, examples of some which provide an unwanted taste within an oral care composition include, for example, cocoamidopropyl betaine and lauryl betaine. The unwanted tastes often associated with these types of surfactants are soapy and chemical. These surfactants are generally included in an oral care composition in a range of about 0.5% to about 5%.

Cationic surfactants useful in the present invention include, for example, derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride or combinations thereof. Additional quaternary ammonium fluorides having detergent properties are described in U.S. Pat. No. 3,535,421 to Briner et al. Of these surfactants, examples of some which provide an unwanted taste within an oral care composition include, for example, cetyl pyridinium chloride or chlorhexidine. The unwanted tastes often associated with these surfactants are chemical and/or antiseptic.

Nonionic surfactants that can be used in the compositions of the present invention include, for example, compounds produced by the condensation of alkylene oxide groups (hydrophilic in nature) with an organic hydrophobic compound which may be aliphatic or alkylaromatic in nature. Examples of suitable nonionic surfactants include the Pluronics® which are poloxamers, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and combinations of such materials.

Flavors

Another component which can be part of an oral care composition includes flavors. Flavors are generally present in an amount of about 0.4% to about 3% by weight of the oral care composition. Examples of some flavors and flavor components used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups. Of these flavors, examples of some which provide an unwanted taste include, for example, citral, geranial, eucalyptol, and eugenol. The unwanted tastes often associated with these types of flavors are sourness, chemical, bitter, pungent, and/or astringent.

Colorants

Additionally, colorants can form part of an oral care composition. Colorants are generally present in an amount of about 0.001% to about 0.5% by weight of the oral care composition. Examples of some colorants used in oral care compositions include D&C Yellow No. 10, FD&C Blue No. 1, FD&C Red No. 40, D&C Red No. 33 and combinations thereof. Levels of the colorant may range from about 0.0001% to about 0.1%. In one embodiment, the colorant is in an amount from about 0.001% to about 0.01% by weight of the oral care composition. Of these colorants, an example of a colorant which provides an unwanted taste includes, for example, D&C Red No. 33. The unwanted tastes often associated with this colorant are metallic and/or chemical.

Sensates

Another component which can be part of an oral care composition is a sensate. Sensate molecules such as cooling, warming, and tingling agents are useful to deliver signals to the consumer. Sensates are generally present in an amount of about 0.001% to about 0.8% by weight of the oral care composition. The most well-known cooling sensate compound is menthol, particularly l-menthol, which is found naturally in peppermint oil. Other isomers of menthol (neomenthol, isomenthol and neoisomenthol) have somewhat similar, but not identical odor and taste, i.e., having disagreeable notes described as earthy, camphor, musty, etc. The biggest difference among the isomers is in their cooling potency. L-menthol provides the most potent cooling, i.e., having the lowest cooling threshold of about 800 ppb, i.e., the concentration level where the cooling effect could be clearly recognized. At this level, there is no cooling effect for the other isomers.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-p-menthan-3-carboxamide. An example of a synthetic carboxamide coolant that is structurally unrelated to menthol is N,2,3-trimethyl-2-isopropylbutanamide. Additional examples of synthetic coolants include alcohol derivatives such as 3-1-menthoxypropane-1,2-diol, isopulegol, and ρ-menthane-3,8-diol; menthone glycerol acetal; menthyl esters such as menthyl acetate, menthyl acetoacetate, menthyl lactate, and monomenthyl succinate. Carboxamide cooling agents are described for example in U.S. Pat. Nos. 4,136,163; 4,150,052; 4,153,679; 4,157,384; 4,178,459 and 4,230,688.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., *J. Pharm. Pharmacol.* (1983), 35:110-112. Of these cooling sensates, examples of some which provide an unwanted taste include, for example, menthol and menthone. The unwanted tastes often associated with these cooling sensates include burning, chemical, and/or medicinal.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%.

Examples of some tingling sensates include, jambu Oleoresin, *Zanthoxylum peperitum*, saanshool-I, saanshool II, sanshoamide, piperine, piperidine, eugenol, spilanthol, 4-(1-methoxymethyl)-2-phenyl-1,3-dioxolane, or combinations thereof. Tingling sensates are generally included in an oral care composition at a level of about 0.0005% to about 1%. Of these tingling sensates, examples of some which provide an unwanted taste within an oral care composition include, for example, jambu, saanshool, and/or eugenol. The unwanted taste(s) often associated with these tingling sensates include a peppery, bitter, and/or metallic taste.

Sweeteners

Another component which can be included in an oral care composition includes a sweetener. Sweeteners can be both natural and artificial and are generally present at about 0.1% to about 1%, by weight of the oral care composition. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a combination of fructose and glucose derived from sucrose), partially hydrolyzed starch, corn syrup solids, dihydrochalcones, monellin, steviosides, glycyrrhizin, or combinations thereof. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame), N-[N-(3,3-dimethylbutyl)-L-α-aspartyl]-L-phenylalanine 1-methyl ester (neotame), and materials described in U.S. Pat. No. 3,492,131, L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used. Of these sweeteners, examples of some which provide an unwanted taste within an oral care composition include, for example, aspartame, saccharin, or neotame. The unwanted taste(s) often associated with these sweeteners include bitterness and sourness.

Actives

An additional component which can be included in an oral care composition includes oral care actives. Oral care actives are generally present in an amount of about 0.0001% to about 8%. Some examples of oral care actives include anticaries agents, antimicrobial agents, antitartar agents, bad breath reduction agents, and bleaching agents. Anticaries agents are generally used in an amount of about 0.01% to about 3.0%. It is common to have a fluoride compound present in dentifrices and other oral compositions in an amount sufficient to give a fluoride ion concentration in the composition of from about 0.0025% to about 5.0% by weight to provide anticaries effectiveness. In one embodiment, the fluoride concentration is from about 0.005% to about 2.0% by weight. A wide variety of fluoride ion-yielding materials can be employed as sources of soluble fluoride in the present compositions and methods. Examples of suitable fluoride ion-yielding materials are found in U.S. Pat. No. 3,535,421 to Briner et al. and U.S. Pat.

No. 3,678,154 to Widder et al. Representative fluoride ion sources include: stannous fluoride, sodium fluoride, potassium fluoride, amine fluoride, sodium monofluorophosphate, indium fluoride, amine fluorides such as Olaflur, and many others. In one embodiment, the anticaries agent comprises stannous fluoride in an amount of about 0.454%. In another embodiment, the anticaries agent comprises sodium fluoride in an amount of about 0.243%. Of these anticaries agents, examples of some which provide an unwanted taste include, for example, stannous fluoride and potassium fluoride. The unwanted tastes often associated with these anticaries agents include earthy, dirty, and/or metallic.

Another oral care active is an antimicrobial agent. One example of an antimicrobial agent is a quaternary ammonium compound. Those useful herein include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl) ammonium bromide, benzyl dimethoylstearyl ammonium chloride, cetylpyridinium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents. Other compounds include bis[4-(R-amino)-1-pyridinium]alkanes as disclosed in U.S. Pat. No. 4,206,215, Jun. 3, 1980 to Bailey. Other quaternary ammonium compounds include the pyridinium compounds. Examples of pyridinium quaternary ammonium compounds include cetylpyridinium and tetradecylpyridinium halide salts (i.e., chloride, bromide, fluoride and iodide). The quaternary ammonium antimicrobial agents can be included at levels of at least about 0.035%. In other embodiments they are included from about 0.045% to about 1.0% or from about 0.05% to about 0.10% by weight of the oral care composition.

The present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, triclosan, triclosan monophosphate, and flavor oils such as thymol. Triclosan and other agents of this type are disclosed in Parran, Jr. et al., U.S. Pat. No. 5,015,466, and U.S. Pat. No. 4,894,220 to Nabi et al. These agents may be present at levels of from about 0.01% to about 1.5%, by weight of the dentifrice composition. Of the above antimicrobial agents, examples of some which provide an unwanted taste include, for example, chlorhexidine, triclosan, and thymol. The unwanted tastes often associated with these types of antimicrobial agents include bitter, dirty, earthy, sour, and/or astringent.

Another oral care active agent includes antitartar agents. One example of an antitartar agent is a pyrophosphate salt as a source of pyrophosphate ion. The pyrophosphate salts useful in the present compositions include, for example, the mono-, di- and tetraalkali metal pyrophosphate salts and combinations thereof. Disodium dihydrogen pyrophosphate ($Na_2H_2P_2O_7$), sodium acid pyrophosphate, tetrasodium pyrophosphate ($Na_4P_2O_7$), and tetrapotassium pyrophosphate ($K_4P_2O_7$) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying embodiments, the amount of pyrophosphate salt is from about 1.5% to about 15%, from about 2% to about 10%, or about 3% to about 8%, by weight of the oral care composition.

An additional example of an oral care active is a bleaching agent. Bleaching agents are generally agents which whiten teeth. Examples of bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. An example of a persulfate includes oxones. The following amounts represent the amount of peroxide raw material, although the peroxide source may contain ingredients other than the peroxide raw material. For example, the peroxide source could be a solution a peroxide raw material and a carrier material. Generally, the present composition may contain from about 0.01% to about 30% of peroxide raw material. In other embodiments, the peroxide raw material is from about 0.1% to about 10% or from about 0.5% to about 5%, by weight of the oral care composition. Of these bleaching agents, examples of some which provide an unwanted taste within an oral care composition include, for example, peroxide and percarbonate. The unwanted tastes often associated with these bleaching agents include dirty, chemical, and/or sour.

Another oral care active is a bad breath reduction agent. These agents generally work to reduce breath malodor. Examples of bad breath reduction agents include copper salts and carbonyl compounds such as ascorbic acid [3-oxo-L-gulofuranolactone]; cis-jasmone [3-methyl-2-(2-pentenyl-2-cyclopentenone]; 2,5-dimethyl-4-hydroxy-3(2H)-furanone; 5-ethyl-3-hydroxy-4-methyl-2(5H)-furanone; vanillin [4-hydroxy-3-methoxybenzaldehyde]; ethyl vanillin; anisaldehyde [4-methoxybenzaldehyde]; 3,4-methylenedioxybenzaldehyde; 3,4-dimethoxybenzaldehyde; 4-hydroxybenzaldehyde; 2-methoxybenzaldehyde; benzaldehyde; cinnamaldehyde [3-phenyl-2-propenal]; hexyl cinnamaldehyde; α-methyl cinnamaldehyde; ortho-methoxy cinnamaldehyde; or combinations thereof. Without being limited by theory, it is believed some bad breath reduction agents work as "traps" by reacting with the thiol or sulfide and forming products with less odor impact. Of these bad breath reduction agents, an example of one which provide an unwanted taste within an oral care composition include, for example, anisaldehyde. Generally, a flavor is not considered a bad breath reduction agent. The unwanted tastes often associated with these types of bad breath reduction agents include chemical, plastic, bitter, and/or sour.

Metal Salts

Another potential component in an oral care composition is a metal salt. Metal salts have a wide range of functions from antimicrobial agents to sensitivity agents and/or buffers. In one embodiment, the metal salt comprises a zinc salt, stannous salt, potassium salt, copper salt, or a combination thereof. In a further embodiment, the zinc salt is selected from the group consisting of zinc fluoride, zinc chloride, zinc iodide, zinc chlorofluoride, zinc acetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, zinc oxide, and combinations thereof. In another embodiment, the zinc salt comprises zinc chloride, zinc citrate, zinc gluconate, zinc lactate, zinc oxide, or combinations thereof.

In an additional embodiment, the potassium salt is selected from the group consisting of potassium nitrate, potassium citrate, potassium oxalate, potassium bicarbonate, potassium acetate, potassium chloride, and combinations thereof. In a further embodiment, the potassium salt comprises potassium nitrate, potassium citrate, potassium chloride, or combinations thereof.

In an additional embodiment, the copper salt is selected from the group consisting of copper fluoride, copper chloride, copper iodide, copper chlorofluoride, copper actetate, copper hexafluorozirconate, copper sulfate, copper lactate, copper tartrate, copper gluconate, copper citrate, copper malate, copper glycinate, copper pyrophosphate, copper metaphosphate, copper oxalate, copper phosphate, copper carbonate, and combinations thereof. In a further embodiment, the copper salt comprises copper gluconate, copper acetate, copper glycinate, or a combination thereof.

In another embodiment, the stannous salt is selected from the group consisting of stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, stannous gluconate, and combinations thereof. In a further embodiment, the stannous salt comprises stannous fluoride, stannous chloride, stannous chloride dihydrate, stannous fluoride, stannous lactate, stannous gluconate, stannous sulfate, or a combination thereof.

Dentifrices containing stannous salts, particularly stannous fluoride and stannous chloride, are described in U.S. Pat. No. 5,004,597 to Majeti et al. Other descriptions of stannous salts are found in U.S. Pat. No. 5,578,293 issued to Prencipe et al. and in U.S. Pat. No. 5,281,410 issued to Lukacovic et al. In addition to the stannous ion source, other ingredients needed to stabilize the stannous may be included, such as the ingredients described in Majeti et al. and Prencipe et al.

Some examples of metal salts which give an off taste include zinc chloride, zinc citrate, copper gluconate, zinc gluconate, or combinations thereof. The off taste associated with these types of metal salts are dirty, dry, earthy, metallic, sour, bitter, and astringent.

The metal salt will be present in an amount from about 0.05% to about 11%, by weight of the oral care composition in one embodiment. In other embodiments, the metal salts are present in an amount of from about 0.5 to about 7% or from about 1% to about 5%. In additional embodiments, the stannous salts are present in an amount of from about 0.1 to about 7% or from about 1% to about 5% or from about 1.5% to about 3% by weight of the oral care composition. In certain embodiments, the amount of zinc or copper salts used in the present invention can range from about 0.01 to about 5%. In other embodiments the amount of zinc or copper salts are from about 0.05 to about 4% or from about 0.1 to about 3.0%.

Miscellaneous

In addition to the above, other components may be included in the oral care compositions to achieve the desired benefit. These miscellaneous components include, for example, chelating agents, abrasives, salivation agents, fillers, solvents, emollients, refractive particles (ex. mica), thickeners, and extracts of natural components.

The oral care composition and its components may contain any combination of elements and properties as disclosed herein.

EXAMPLES

Consumer Test I

In order to show the effect of the addition of a TRPV1 activator and/or Vanitrope on the perception of taste in an oral care composition, the following compositions are made and given to consumers to sample.

|  | Control | +VBE | +Vanitrope | +Zingerone |
|---|---|---|---|---|
| Zinc citrate dihydrate | 0.79 | 0.79 | 0.79 | 0.79 |
| Sodium Citrate tribasic dihydrate | 0.27 | 0.27 | 0.27 | 0.27 |
| Sodium Fluoride | 0.24 | 0.24 | 0.24 | 0.24 |
| Stannous Chloride Dihydrate | 0.21 | 0.21 | 0.21 | 0.21 |
| Sorbitol (70%) | 45.00 | 45.00 | 45.00 | 45.00 |
| Sodium Saccharin | 0.25 | 0.25 | 0.25 | 0.25 |
| Vanitrope |  |  | 0.04 |  |
| Zingerone |  |  |  | 0.04 |
| VBE |  | 0.003 |  |  |
| Hydroxyethyl cellulose 250M | 0.30 | 0.30 | 0.30 | 0.30 |
| Sodium Carboxymethylcellulose | 1.30 | 1.30 | 1.30 | 1.30 |
| Carrageenan Mixture | 0.70 | 0.70 | 0.70 | 0.70 |
| Titanium Dioxide, Anatase | 0.53 | 0.53 | 0.53 | 0.53 |
| Hydrated Silica amorphous Z119 | 17.00 | 17.00 | 17.00 | 17.00 |
| Sodium Alkyl Sulfate (28%) | 5.00 | 5.00 | 5.00 | 5.00 |
| Flavor | 1.00 | 1.00 | 1.00 | 1.00 |
| Water Purified, USP | QS | QS | QS | QS |

The base of the control dentifrice (i.e. everything but the flavor) is made via vacuum mixing. The flavor is added in a second step my speed mixing to complete the control. The additional compositions are then made by speed mixing into the control base the TRPV1 activator and/or vanitrope plus flavor at the stated levels. The samples are then placed in tubes and delivered to the testing facility.

At the testing facility, panelists are provided with a generic brush with 1.0 g of toothpaste. Each panelist has an individual sink, mirror, disposable cup and paper towels. They are asked to brush as they normally would at home. Before and after brushing the panelist will answer a series of questions relating to their experience with the toothpaste. The panelists are asked to comment on their experience right after brushing and then at each hour interval for three hours. The comments from the consumers are translated into numerical values for comparison. The results for the above compositions as it related to bothersome and bad aftertaste are shown below.

|  | Control | +VBE | +Zingerone | +Vanitrope |
|---|---|---|---|---|
| Bothersome (Hr 1) | 2.5 | 0.8 | 1.1 | 1.5 |
| Bothersome (Hr 2) | 1.2 | 0.4 | 0.6 | 0.7 |
| Bothersome (Hr 3) | 0.7 | 0.3 | 0.4 | 0.4 |
| Bad Aftertaste (Hr 1) | 2.4 | 1.0 | 1.8 | 1.5 |
| Bad Aftertaste (Hr 2) | 1.0 | 0.4 | 0.5 | 0.9 |
| Bad Aftertaste (Hr 3) | 0.5 | 0.2 | 0.3 | 0.5 |

As can be seen from the above chart, each of the TRPV1 activators (VBE and zingerone) showed an improved taste over the control for both bothersome and bad aftertaste for each of hours 1-3 while vanitrope showed a taste improvement for hours 1-3 for bothersome and hours 1-2 for bad aftertaste.

Also included in the above testing are combinations of TRPV1 activators and/or vanitrope. The formulations for these tests are below and the control is the same as that listed above.

|  | +VBE and Vanitrope | +Vanitrope and Zingerone | +Zingerone and VBE | +VBE and Zingerone and Vanitrope |
|---|---|---|---|---|
| Zinc citrate dehydrate | 0.79 | 0.79 | 0.79 | 0.79 |
| Sodium Citrate tribasic dihydrate | 0.27 | 0.27 | 0.27 | 0.27 |
| Sodium Fluoride | 0.24 | 0.24 | 0.24 | 0.24 |
| Stannous Chloride Dihydrate | 0.21 | 0.21 | 0.21 | 0.21 |
| Sorbitol (70%) | 45.00 | 45.00 | 45.00 | 45.00 |
| Sodium Saccharin | 0.25 | 0.25 | 0.25 | 0.25 |
| Vanitrope | 0.04 | 0.04 |  | 0.02 |
| Zingerone |  | 0.04 | 0.04 | 0.02 |
| VBE | 0.003 |  | 0.003 | 0.006 |
| Hydroxyethyl cellulose 250M | 0.30 | 0.30 | 0.30 | 0.30 |
| Sodium Carboxymethyl-cellulose | 1.30 | 1.30 | 1.30 | 1.30 |
| Carrageenan Mixture | 0.70 | 0.70 | 0.70 | 0.70 |
| Titanium Dioxide, Anatase | 0.53 | 0.53 | 0.53 | 0.53 |
| Hydrated Silica amorphous Z119 | 17.00 | 17.00 | 17.00 | 17.00 |
| Sodium Alkyl Sulfate (28%) | 5.00 | 5.00 | 5.00 | 5.00 |
| Flavor | 1.00 | 1.00 | 1.00 | 1.00 |
| Water Purified, USP | QS | QS | QS | QS |

The results for the above compositions are shown below.

|  | Control | Vanitrope + VBE | Vanitrope + Zingerone | Vanitrope + Zingerone + VBE | Zingerone + VBE |
|---|---|---|---|---|---|
| Bothersome (Hr 1) | 2.5 | 0.9 | 2.0 | 1.6 | 1.2 |
| Bothersome (Hr2) | 1.2 | 0.2 | 1.1 | 0.8 | 0.5 |
| Bothersome (Hr3) | 0.7 | 0.1 | 0.6 | 0.7 | 0.1 |
| Bad Aftertaste (Hr1) | 2.4 | 0.8 | 0.8 | 1.4 | 0.9 |
| Bad Aftertaste (Hr2) | 1.0 | 0.2 | 0.2 | 0.3 | 0.5 |
| Bad Aftertaste (Hr3) | 0.5 | 0.1 | 0.1 | 0.3 | 0.2 |

As can be seen from the above results, the various combinations of TRPV1 activators and/or vanitrope showed an improvement over the control in both bothersome and bad taste at all of hours 1-3 except the combination of all 3 which showed an equivalent taste at hour 3. Thus, when comparing to the results of the individual TRPV1 activators or vanitrope above, while VBE tends to give to best result at hour 1, some of the combinations give better results at hours 2 and 3, depending on the measurement used. Interestingly, however, the combination of vanitrope, zingerone, and VBE, while not getting the best results in the testing as to reduction of bothersome or bad aftertaste, seems to have a preferred taste to the consumer over the other combinations tried. Thus, while it is not the best at reducing off taste, consumers seem to prefer it.

Additional panel testing with rinses made with VBE and long lasting coolants shows that the compositions containing VBE provide longer lasting pleasant sensory experiences, which are described as less sourness and cooling. Rinses made with CPC and lower levels of ethanol could still provide an ethanol like clean signal due to the VBE.

Example Product I

Metal Salt Containing Dentifrice

The dentifrices are made using conventional methods and are shown below with amounts in weight %.

| Ingredient | IA | IB | IC | ID | IE |
|---|---|---|---|---|---|
| Calcium Carbonate | | | | 40.00 | |
| Binders | 1.00 | 1.8 | 1.00 | 1.00 | 0.20 |
| Thickeners | 2.00 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.00 | 1.00 | 1.00 | 1.00 | 1.00 |
| Coolants | 0.03 | 0.24 | 0.20 | 0.50 | 0.58 |
| VBE | 0.01 | 0.01 | 0.01 | 0.01 | 0.01 |
| Glycerin USP | 16.489 | | 15.00 | | |
| Poloxamer 407 NF | | | | | 0.20 |
| Monosodium Orthophosphate | | | | | |
| Potassium Nitrate | 5.00 | | | | |
| Saccharin Sodium USP | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | 1.00 | | | |
| Sodium Monofluorophosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |
| Humectant | 10.50 | 33.00 | 12.00 | 14.00 | 57.00 |
| Tetra Sodium Pyrophosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

| Ingredient | IF | IG | IH | IJ | IK |
|---|---|---|---|---|---|
| Calcium Carbonate | | | | 40.00 | |
| Binders | 1.00 | 1.8 | 1.00 | 1.00 | 0.20 |
| Thickeners | 0.5 | 1.00 | 1.25 | 0.4 | 0.8 |
| Color Solution (1%) | 0.05 | 0.05 | | | 0.175 |
| Dibasic Calcium Phosphate Dihydrate | | | 35.00 | | |
| Flavor[1] | 1.5 | 1.0 | 0.8 | 1.00 | 0.8 |
| Coolants | 0.5 | 0.2 | | 0.08 | |
| VBE | | | 0.01 | | |
| Capsaicin | 0.001 | | | | |
| Piperine | | 0.002 | | | |
| Vanitrope | | | 0.06 | 0.10 | |
| Zingerone | | | 0.04 | | |
| Glycerin USP | 16.489 | | 15.00 | | 0.10 |
| Potassium Nitrate | 5.00 | | | | |
| Saccharin Sodium USP | 0.47 | 0.25 | 0.30 | 0.300 | 0.58 |
| Silica Abrasive | 24.00 | 12.50 | | | 17.00 |
| Sodium Lauryl Sulfate (27.9% soln) | 7.50 | 7.00 | 5.50 | 7.00 | 4.00 |
| NaOH 50% Solution | | 1.00 | | | |
| Sodium Monofluorophosphate | 0.76 | | 0.76 | 0.76 | 0.76 |
| Sodium Fluoride | | 0.32 | | | |
| Sodium Gluconate | | 1.00 | | | |
| Stannous Chloride Dihydrate | | 1.00 | | | |
| Zinc Citrate | | 0.50 | | | |
| Sodium Phosphate, Tribasic | 3.20 | | | | |
| Humectant | 12.00 | 33.00 | 12.00 | 14.00 | 57.00 |
| Tetra Sodium Pyrophosphate, Anhydrous | | | 0.50 | 0.50 | 3.85 |
| Sodium Acid Pyrophosphate | | | | | 1.00 |
| Titanium Dioxide | 0.50 | 0.50 | | | 0.25 |
| Water, Purified, USP | QS | QS | QS | QS | QS |

[1]Flavor comprises about 31.3% menthol supplying about 500 ppm menthol.

Example Product II

Mouth Rinse Compositions

Mouth rinse compositions are made using conventional methods and are shown below with amounts of components in weight %.

| Ingredient | IIA | IIB | IIC |
|---|---|---|---|
| Ethanol, USP 190 proof | 15.000 | 15.000 | 15.000 |
| Glycerin | 7.500 | 7.500 | 7.500 |
| Polysorbate 80, NF | 0.120 | 0.120 | 0.120 |
| Flavor | 0.160 | 0.160 | 0.160 |
| Saccharin Sodium | 0.067 | 0.067 | 0.060 |
| Color Solution | 0.040 | 0.040 | 0.040 |
| VBE | 0.003 | 0.005 | 0.001 |
| Zingerone | | | 0.01 |
| Vanitrope | 0.008 | | 0.005 |
| Cetylpyridinium Chloride | 0.045 | 0.045 | 0.045 |
| Benzoic Acid | 0.005 | 0.005 | 0.005 |
| Sodium Benzoate | 0.054 | 0.054 | 0.054 |
| Water | QS | QS | QS |

Example Product III

Peroxide Mouth Rinse Compositions

Peroxide-containing mouth rinse compositions are shown below with amounts of components in weight %. These compositions are made using conventional methods. The mouth rinse compositions provide a pleasant high-impact minty taste during use and noticeable long-lasting fresh breath.

| Ingredient | IIIA | IIIB | IIIC | IIID | IIIE | IIIF |
|---|---|---|---|---|---|---|
| 35% $H_2O_2$ solution | 4.286 | 4.286 | 4.286 | 2.143 | 4.286 | 4.286 |
| Coolant | 0.075 | 0.02 | 0.04 | 0.04 | 0.03 | 0.04 |
| VBE | | 0.003 | | 0.005 | 0.01 | 0.005 |
| Capsaicin | 0.0003 | | | | | 0.00001 |
| Piperine | 0.0001 | | | | | 0.00001 |
| Zingerone | | | 0.005 | 0.002 | | 0.004 |
| Vanitrope | | | 0.008 | 0.002 | | 0.005 |
| Flavor | 0.145 | 0.135 | 0.135 | 0.15 | 0.135 | 0.135 |
| Calcium Chloride | 0.025 | | 0.025 | 0.02 | 0.025 | 0.025 |
| Poloxamer 407 | 0.75 | 0.75 | 0.750 | 0.10 | 0.10 | 0.10 |
| Glycerin | 11.00 | 11.00 | 11.00 | 20.00 | 20.00 | 20.00 |
| Propylene Glycol | 3.00 | 3.00 | | 4.00 | 4.00 | 4.00 |
| Sucralose | | 0.05 | — | | | |
| Sodium Saccharin | 0.08 | — | 0.068 | 0.06 | 0.08 | 0.06 |
| Polyphosphate | | | 1.00 | | | |
| Phytic Acid | | 2.00 | | | | |
| Cetyl Pyridinium Chloride | | | | 0.074 | 0.10 | 0.10 |
| Na Citrate | 0.212 | 0.212 | | | | |
| Citric Acid | 0.052 | 0.052 | 0.052 | | | |
| Alcohol, USP | | | 5.00 | | | |
| Water, Purified, USP | QS | QS | QS | QS | QS | QS |

Example Product IV

Tartar Control Dentifrice Compositions

The dentifrices are made using conventional methods and are shown below with amounts in weight %.

| Ingredient | VA | VB | VC | VD | VE |
|---|---|---|---|---|---|
| Calcium Peroxide FCC | | | 0.10 | | |
| Thickener | 5.0 | 2.5 | 4.5 | 0.80 | 5.0 |
| Binder | 0.60 | 0.75 | 0.40 | 0.45 | 0.70 |
| Polymer | | | 0.20 | | |

-continued

| Ingredient | VA | VB | VC | VD | VE |
|---|---|---|---|---|---|
| Color Solution (1%) | 0.05 | 0.05 | 0.50 | 0.75 | 0.175 |
| Flavor | | | | | 0.15 |
| Coolant | | | 0.02 | 0.05 | 0.02 |
| VBE | 0.01 | 0.05 | 0.005 | | 0.001 |
| Capsaicin | | | | 0.005 | |
| Piperine | | | 0.005 | | |
| Zingerone | 0.02 | | 0.01 | 0.02 | |
| Vanitrope | 0.02 | 0.08 | 0.04 | 0.08 | |
| Glycerin USP 99.7% | 9.00 | 11.85 | 33.164 | 9.00 | |
| Poloxamer 407 NF | | | 1.00 | | 0.20 |
| Tetra Potassium Pyrophosphate (60% Soln) | 6.38 | | | | |
| Propylene Glycol USP Crest | | | 10.00 | | |
| Saccharin Sodium USP Granular | 0.46 | 0.50 | 0.45 | 0.40 | 0.58 |
| Sodium Acid Pyrophosphate | 2.10 | | | 4.00 | 1.00 |
| Silica Abrasive | 22.00 | 31.00 | 20.00 | 21.00 | 17.00 |
| Silica Thickening | | | 2.00 | | |
| Sodium Bicarbonate USP | | 1.50 | 9.00 | | |
| Sodium Carbonate Anhydrous NF | | 0.50 | | | |
| Sodium Hydroxide 50% Solution | | | 1.74 | 2.20 | |
| Sodium Lauryl Sulfate (27.9% soln) | 4.00 | 5.00 | 3.00 | 4.00 | 4.00 |
| Sodium Monofluorophosphate | 0.76 | 0.76 | 0.76 | 0.76 | 0.76 |
| Sorbitol Solution USP | 24.28 | 24.54 | 3.985 | 44.686 | 56.885 |
| Tetra Sodium Pyrophosphate, Anhydrous | 2.05 | 5.045 | 3.85 | | 3.85 |
| Titanium Dioxide | 0.50 | | 1.00 | | 0.25 |
| Titanium Dioxide/Carnauba Wax Prills | | 0.60 | | 0.30 | |
| Water, Purified, USP | QS | QS | QS | QS | QS |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for improving taste of an oral care composition, comprising:
   mixing into an oral care composition, vanitrope; from about 0.001% to about 0.025% by weight of the composition, vanillyl butyl ether; from about 0.01% to about 0.15%, by weight of the composition, zingerone; and from about 0.05% to about 11%, by weight of the composition, metal salt selected from the group consisting of a zinc salt, stannous salt, potassium salt, copper salt, and mixtures thereof.

2. The method of claim 1, further comprising adding capsaicin, capsiate, shoagol, gingerol, piperine, or a combination thereof, to the oral care composition.

3. The method of claim 1, further comprising adding to the oral care composition a TRPV1 enhancer selected from the group consisting of damascone, geranyl butyrate, 2-octanone, furfural, ionone, 2,6-dimethyl-5-heptenal, tetrasodium pyrophosphate, alpha dimethyl phenethyl acetate, phenylacetaldehyde dimethyl acetal, kephalis, linalool oxide, carvyl acetate, farnesene, trans-2-hexenyl acetate, heptyl alcohol, and combinations thereof.

4. The method of claim 1, wherein the vanillyl butyl ether is present in an amount from 0.002% to 0.02% by weight of the oral care composition.

5. The method of claim 1, wherein the stannous salt is present and is selected from the group consisting of stannous fluoride, stannous chloride, stannous iodide, stannous chlorofluoride, stannous actetate, stannous hexafluorozirconate, stannous sulfate, stannous lactate, stannous tartrate, stannous gluconate, stannous citrate, stannous malate, stannous glycinate, stannous pyrophosphate, stannous metaphosphate, stannous oxalate, stannous phosphate, stannous carbonate, and combinations thereof.

6. The method of claim 1, wherein the zinc salt is present and is selected from the group consisting of zinc fluoride, zinc chloride, zinc iodide, zinc chlorofluoride, zinc acetate, zinc hexafluorozirconate, zinc sulfate, zinc lactate, zinc tartrate, zinc gluconate, zinc citrate, zinc malate, zinc glycinate, zinc pyrophosphate, zinc metaphosphate, zinc oxalate, zinc phosphate, zinc carbonate, zinc oxide, and combinations thereof.

7. The method of claim 1, wherein the potassium salt is present and is selected from the group consisting of potassium nitrate, potassium citrate, potassium oxalate, potassium bicarbonate, potassium acetate, potassium chloride, and combinations thereof.

8. The method of claim 1, wherein the vanitrope is present in an amount from about 0.01% to about 0.15% by weight of the oral care composition.

9. The method of claim 1, wherein the metal salt is zinc citrate and wherein the metal salt is present in an amount from about 0.05% to about 5.0% by weight of the oral care composition.

10. The method of claim 1, wherein vanitrope is present in an amount from about 0.05% to about 0.15% by weight of the oral care composition.

11. The method of claim 1, wherein the oral care composition further comprises from about 5% to about 80% by weight water.

12. The method of claim 1, wherein from about 0.006% to about 0.025%, by weight of the composition, of vanillyl butyl ether is added.

13. The method of claim 1, wherein from about 0.02% to about 0.04%, by weight of the composition, of vanitrope is added.

14. The method of claim 1, wherein from about 0.02% to about 0.04%, by weight of the composition, of zingerone is added.

15. The method of claim 1, wherein the metal salt is zinc citrate.

16. A method for improving taste of an oral care composition, comprising: mixing from about 0.02% to about 0.04%, by weight of the composition, of vanitrope; from about 0.001% to about 0.025% by weight of the composition, vanillyl butyl ether; from about 0.02% to about 0.04%, by weight of the composition, zingerone; and zinc citrate.

* * * * *